United States Patent
Malladi et al.

(10) Patent No.: US 7,179,624 B2
(45) Date of Patent: Feb. 20, 2007

(54) **ECO FRIENDLY PROCESS FOR THE PREPARATION OF CHIRAL ALCOHOLS BY ASYMMETRIC REDUCTION OF PROCHIRAL KETONES IN WATER USING SOAKED *PHASEOLUS AUREUS* L (GREEN GRAMS)**

(75) Inventors: Pardhasaradhi Malladi, Andhra Pradesh (IN); Kumaraswamy Gullapalli, Andhra Pradesh (IN); Ramesh Sunkanapally, Andhra Pradesh (IN); Chembumkulam Kamalakshyamma Snehalatha Nair, Andhra Pradesh (IN); Arun Kanti Das, Andhra Pradesh (IN)

(73) Assignee: Council of Scientific and Industrial Research, New Delhi (IN)

( * ) Notice: Subject to any disclaimer, the term of this patent is extended or adjusted under 35 U.S.C. 154(b) by 116 days.

(21) Appl. No.: 10/395,885

(22) Filed: Mar. 25, 2003

(65) Prior Publication Data

US 2004/0191879 A1    Sep. 30, 2004

(51) Int. Cl.
    *C12P 7/02*    (2006.01)
(52) U.S. Cl. ............... 435/155; 424/757; 424/725
(58) Field of Classification Search ......... 514/732, 514/724, 675, 682, 568, 328; 424/757; 435/155
    See application file for complete search history.

(56) References Cited

U.S. PATENT DOCUMENTS 6,218,581 B1 *    4/2001    Nagaoka .................. 568/648

OTHER PUBLICATIONS

Cheanyeh et al, "Glucose Metabolism and Bioreduction of 2-butanone by Candida Utilis Studied by Means of Ion-Exchange Chromatography", Journal of Chromatography A, Elsevier Science, NL., vol. 763, No. 1-2, 28 Feb. 28, 1997, pp. 205-211, XP004116736.

Giri et al, "Biotransformations Using Plant Cells, Organ Cultures and Enzyme Systems: Current Trends and Future Prospects", Biotechnology Advances, Elsevier, Publishing, Barking, GB, vol. 19, No. 3, Jun. 2001, pp. 175-199.

Nakamura et al., "Cyanobacterium-catalyzed Asymmetric Reduction of Ketones", Tetrahedron Letters, Elsevier Science Publishers, Amsterdam, NL, vol. 41, No. 35, Aug. 2000, pp. 6799-6802, XP004213952.

* cited by examiner

*Primary Examiner*—Leon B. Lankford, Jr.
*Assistant Examiner*—Allison M. Ford
(74) *Attorney, Agent, or Firm*—Nixon & Vanderhye PC

(57) ABSTRACT

The present invention relates to a new eco-friendly process for the preparation of chiral alcohols by asymmetric reduction of prochiral ketones in water using soked *phaseolus aureus* L (green grams).

6 Claims, No Drawings

ECO FRIENDLY PROCESS FOR THE PREPARATION OF CHIRAL ALCOHOLS BY ASYMMETRIC REDUCTION OF PROCHIRAL KETONES IN WATER USING SOAKED *PHASEOLUS AUREUS* L (GREEN GRAMS)

FIELD OF THE INVENTION

The present invention relates to a new eco-friendly process for the preparation of chiral alcohols by asymmetric reduction of prochiral ketones in water using soked *phaseolus aureus* L (green grams).

BACKGROUND OF THE INVENTION

Chiral alcohols are well known intermediates having good demand as precursors in the development of pharmaceutically important drugs and agrochemicals. Key intermediates can be obtained by resolution of the recemate by chemical as well as by biochemical methods. In procedures which involve resolution of the racemate there is always 50% of the unwanted enantiomer. Hence, it is important to develop methods of asymmetric synthesis which do not allow for the formation of the unwanted enantiomer (50%). Asymmetric reduction of prochiral ketones to give a single enantiomer is one solution to this problem.

Asymmetric reduction of prochiral ketones by chemical methods involve use of expensive chiral reagents. Biocatalytic approach is the most suitable method for preparation of a wide range of chiral alcohols. Baker's yeast is by far the most widely used microorganism for reduction of prochiral ketones to the corresponding optically active alcohols. Here, recovery of desired product from emulsion is cumbersome and at times use of costly co-factors become necessary. These co-factors have to be subsequently regenarated.

Plant cell cultures represent an important potential to perform biochemical reaction on organic compounds. Most of these reactions so for, have been confined to the biotransformation of secondary metabolites produced by plant cell. There have been a few examples of the biotransformation of synthetically important foreign substrates (*Tetrahedron Asymmetry* 1996, 7, 1571).

Baldassarre et al., have reported the use of whole plant cell for the asymmetric reduction of prochiral ketones (*J. Mol. Catal. B: Enzym.* 2000, 11, 55–58). Use of immobilized plant cell cultures as potential biocatalyst for the transformation of synthetically important foreign substrate was also investigated (*Phytochemistry* 1991, 30, 3595, *Phytochemistry* 1994, 35, 661).

In our attempts to produce chiral alcohols in high enantiomeric excess and high yield, we have investigated several soaked edible grams as potential biocatalysts for the asymmetric reduction of prochiral ketones. We found for the first time that the soaked *phaseolus aureus* L (green grams) could be effectively used as biocatalyst for the asymmetric reduction of prochiral ketones to obtain chiral alcohols in moderate yields with good enantiomeric selectivity, whereas *phaseolus mungo* L (black grams) and *cicer arietinum* L (bengal grams) gave low enantioselectivity with a negligable yield.

OBJECTS OF THE INVENTION

The main object of the invention is to provide a process for obtaining chiral alcohol with high enantiomeric excess in good yields and amenable for scale up operation due to ease of work up.

It is another object of the invention to provide a process for the production of chiral alcohol wherein the isolation of the product is easy with no slush formation.

It is a further object of the invention to provide a process for the production of chiral alcohol using *Phaseolus aureus* L (green gram) as easily available biocatalyst.

It is yet another object of the invention to provide an eco-friendly process in which the soaked *phaseolus aureus* L (green gram) can be used as manure after reaction.

SUMMARY OF THE INVENTION

The above objects of the invention are achieved by a process to prepare chiral alcohols of the formula (II)

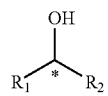

II where $R_1$ represents methyl and $R_2$ represents phenyl, substituted phenyl or benzyl, 1-naphthalenol of the formula (IV)

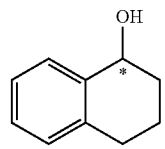

IV and 1,3-diphenyl propan-1-ol of the formula (VI)

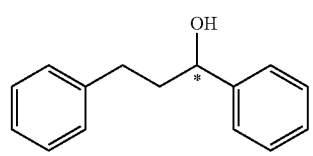

VI by the use of soaked *vigna radiata* (green grams) as biocatalyst in the asymmetric reduction of prochiral ketones of the formula (I) wherein $R_1$ and $R_2$ have the same meaning as

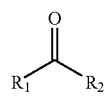

I mentioned above; 1-naphthalenone of the formula (III) and chalcone of the formula (V)

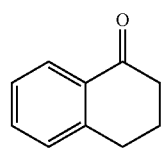

III

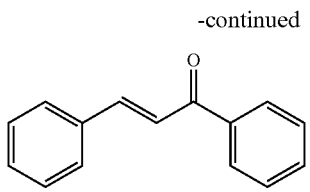

V

Accordingly, the present invention provides a new eco-friendly process for the preparation of chiral alcohols, with high enantiomeric excess and good yields, which comprises soaking of the *phaseolus aureus* L (green grams) in water, reacting the prochiral ketones with the soaked *phaseolus aureus* L (green grams) in water, filtering the contents, extraction of the chiral alcohol into an organic solvent and its isolation through column chromatography.

In an embodiment of the present invention *phaseolus aureus* L (green grams) was soaked in deionised water for a period in the range of 20–25 hr.

In another embodiment of the present invention prochiral ketones were reacted with the soaked *phaseolus aureus* L (green grams) in water using a shaker for agitation for a period in the range of 20–50 hr at a temperature in the range of 14–30° C.

DETAILED DESCRIPTION OF THE INVENTION

Washed *phaseolus aureus* L (green grams) (50–500 g.) were taken into a conical flask and allowed to soak in deionised water (400 ml) for a period in the range of 20–25 hr. Prochiral ketone (500 mg–5 g) was added to the soaked *phaseolus aureus* L (green grams) in the above water, covered and allowed to shake for a period in the range of 24–50 hr at a temperature in the range 14–30° C. Then, the green grams were filtered off and washed with deionised water.

The combined filtrate was extracted with an organic solvent. Organic layer was washed, dried and the crude product isolated. Pure chiral alcohol was obtained with high enantiomeric excess after column chromatography with silica gel using chloroform as eluant.

The following examples are given by way of illustration of the present invention and therefore should not be construed to limit the scope of the present invention.

EXAMPLE 1

Washed *phaseolus aureus* L (green grams) 50 g. were taken into a conical flask and allowed to soak in deionised water (400 ml) for a period of 24 hr. Acetophenone (0.500 g; 0.004 moles) I(a) was added to the soaked *phaseolus aureus* L (green grams) in the above water, covered and allowed to shake for 24 hr at 15–20° C. Then the green grams were filtered off and washed with deionised water (3×100 ml). The combined filtrate was extracted with chloroform (3×500 ml). The chloroform layer was dried and the crude product obtained (360 mg). Pure 1-phenyl-(1S)-ethan-1-ol II(a) was obtained after column chromatography with silica gel using chloroform as eluent.

Yield: 0.255 g, 50%; ee: 84%; ($[\alpha]^{25}_D$=−37.8°, c=1, methanol)

EXAMPLE 2

Washed *phaseolus aureus* L (green grams) 50 g. were taken into a conical flask and allowed to soak in deionised water (400 ml) for a period of 24 hr. 4-chloroacetophenone (0.500 g; 0.0032 moles) I(b) was added to the soaked *phaseolus aureus* L (green grams) in the above water, covered and allowed to shake for 24 hr at 15–20° C. Then the green grams were filtered off and washed with deionised water (3×100 ml). The combined filtrate was extracted with chloroform (3×500 ml). The chloroform layer was dried and the crude product obtained (340 mg). Pure 1-(4-chlorophenyl-(1S)-ethan-1-ol II(b) was obtained after column chromatography with silica gel using chloroform as eluent.

Yield: 0.253 g, 50%; ee: 89.76%; ($[\alpha]^{25}_D$=−38.6°, c=1, chloroform).

EXAMPLE 3

Washed *phaseolus aureus* L (green grams) 50 g. were taken into a conical flask and allowed to soak in deionised water (400 ml) for a period of 24 hr. 4-methylacetophenone (0.500 g; 0.0037 moles) I(c) was added to the soaked *phaseolus aureus* L (green grams) in the above water, covered and allowed to shake for 24 hr at 15–20° C. Then the green grams were filtered off and washed with deionised water (3×100 ml). The combined filtrate was extracted with chloroform (3×500 ml). The chloroform layer was dried and the crude product obtained (340 mg). Pure 1-(4-methylphenyl-(1S)-ethan-1-ol II(c) was obtained after column chromatography with silica gel using chloroform as eluent;

Yield: 0.254 g, 50%; ee: 94.54%; ($[\alpha]^{25}_D$=−48.5°, c=1, chloroform).

EXAMPLE 4

Washed *phaseolus aureus* L (green grams) 50 g. were taken into a conical flask and allowed to soak in deionised water (400 ml) for a period of 24 hr. Phenylacetone (0.500 g; 0.0037 moles) I(d) was added to the soaked *phaseolus aureus* L (green grams) in the above water, covered and allowed to shake for 24 hr at 15–20° C. Then the green grams were filtered off and washed with deionised water (3×100 ml). The combined filtrate was extracted with chloroform (3×500 ml). The chloroform layer was dried and the crude product obtained (330 mg). Pure 1-phenyl-(2S)-propan-2-ol II(d) was obtained after column chromatography with silica gel using chloroform as eluent.

Yield: 0.232 g, 45.67%; ee: 97.86%; ($[\alpha]^{25}_D$=+32.62°, c=1, chloroform).

EXAMPLE 5

Washed *phaseolus aureus* L (green grams) 50 g. were taken into a conical flask and allowed to soak in deionised water (400 ml) for a period of 24 hr. 1-naphthalenone (0.500 g; 0.0034 moles) III was added to the soaked *phaseolus aureus* L (green grams) in the above water, covered and allowed to shake for 46 hr at 15–20° C. Then the green grams were filtered off and washed with deionised water (3×100 ml). The combined filtrate was extracted with chloroform (3×500 ml). The chloroform layer was dried and the crude product obtained (480 mg). Pure (1S)-1,2,3,4-tetrahydro-1-naphthalenol (IV) was obtained after column chromatography with silica gel using chloroform as eluent.

Yield: 0.259 g, 51%; ee: 98.43%; ($[\alpha]^{25}_D$=+31.5°, c=1, chloroform).

EXAMPLE 6

Washed *phaseolus aureus* L (green grams) 50 g. were taken into a conical flask and allowed to soak in deionised water (400 ml) for a period of 24 hr. Chalcone (0.500 g; 0.0024 moles) (V) was added to the soaked *phaseolus aureus* L (green grams) in the above water, covered and allowed to shake for 24 hr at 15–20° C. Then the green grams were filtered off and washed with deionised water (3×100 ml). The combined filtrate was extracted with chloroform (3×500 ml). The chloroform layer was dried and the crude product obtained (240 mg). Pure 1,3-diphenyl-(1S)-propan-1-ol (VI) was obtained after column chromatography with silica gel using chloroform as eluent.

Yield: 0.141 g, 28%; ee: 85.62%; ($[\alpha]^{25}_D$=+28°, c=1, dichloromethane)

EXAMPLE 7

Washed *phaseolus aureus* L (green grams) 500 g. were taken into a conical flask and allowed to soak in deionised water (4 L) for a period of 24 hr. Acetophenone (5 g; 0.0416 moles) I(a) was added to the soaked *phaseolus aureus* L (green grams) in the above water, covered and allowed to shake for 24 hr at room temperature (28° C). Then the green grams were filtered off and washed with deionised water (5×600 ml). The combined filtrate was extracted with chloroform (30×500 ml). The chloroform layer was dried and the crude product obtained (3.21 g.). Pure 1-phenyl-(1S)-ethan-1-ol II(a) was obtained after column chromatography with silica gel using chloroform as eluent.

Yield: 2.08 g, 40%; ee: 71.44%; ($[\alpha]^{25}_D$=–32.13°, c=1, methanol).

Comparitive Examples

EXAMPLE 8

Washed *phaseolus mungo* L (black grams) 50 g. were taken into a conical flask and allowed to soak in deionised water (400 ml) for a period of 24 hr. Acetophenone (0.500 g; 0.004 moles) I(a) was added to the soaked *phaseolus mungo* L (black grams) in the above water, covered and allowed to shake for 24 hr at room temperature (28° C). Then the black grams were filtered off and washed with deionised water (3×100 ml). The combined filtrate was extracted with chloroform (3×500 ml). The chloroform layer was dried and the crude product obtained (0.1 g.). Pure 1-phenyl-(1S)-ethan-1-ol II(a) was obtained after column chromatography with silica gel using chloroform as eluent.

Yield: 0.020 g, 4%; ee: 23.11%; ($[\alpha]^{25}_D$=–10.4°, c=1, methanol).

EXAMPLE 9

Washed *cicer arietinum* L (bengal grams) 50 g. were taken into a conical flask and allowed to soak in deionised water (400 ml) for a period of 24 hr. Acetophenone (0.500 g; 0.004 moles) I(a) was added to the soaked *cicer arietinum* L (bengal grams) in the above water, covered and allowed to shake for 24 hr at room temperature (28° C). Then the green grams were filtered off and washed with deionised water (3×100 ml). The combined filtrate was extracted with chloroform (3×500 ml). The chloroform layer was dried and the crude product obtained (80 mg.). Pure 1-phenyl-(1S)-ethan-1-ol II(a) was obtained after column chromatography with silica gel using chloroform as eluent.

Yield: 0.010 g, 2%; ee: 8%; ($[\alpha]^{25}_D$=–3.6°, c=1, methanol).

The Main Advantages of the Present Invention are

1) The process produced chiral alcohol with high enantiomeric excess in good yields and amenable for scale up operations since workup and isolation of the product is easy with no slush formation.

2) *Phaseolus aureus* L (green gram) used as biocatalyst is easily available.

3) The process is ecofriendly and the soaked *phaseolus aureus* L (green gram) can be used as manure after reaction.

We claim:

1. A process for the preparation of a chiral alcohol comprising:

soaking *Phaseolus aureus* L in deionized water for a period ranging from 20–25 hours prior to reaction with a prochiral ketone, reacting the prochiral ketone with *Phaseolus aureus* L soaked in water to form a reaction mixture, filtering the reaction mixture, extracting chiral alcohol produced thereby into an organic solvent, and isolating the chiral alcohol so obtained.

2. A process as claimed in claim 1 wherein the isolation is carried out by column chromatography.

3. A process as claimed in claim 1 wherein the prochiral ketone is reacted with the *Phaseolus aureus* L soaked in water using a shaker for agitation for a period in the range of 20–50 hrs at a temperature in the range of 14–30° C.

4. A process as claimed in claim 1 wherein the prochiral ketone used is selected from the group consisting of acetophenone, 4-chloroacetophenone, 4-methylacetophenone, phenylacetone, 1, 2, 3, 4-tetrahydro-1-naphthalenone and chalcone.

5. A process as claimed in claim 1 wherein the chiral alcohol is (1S) 1,2,3,4-tetrahydro-1-naphthalenol.

6. A process as claimed in claim 1 wherein the organic solvent used for extraction of the chiral alcohol comprises chloroform.

* * * * *